United States Patent [19]

Trammell et al.

[11] 4,407,280
[45] Oct. 4, 1983

[54] DISPOSABLE HOOD

[76] Inventors: W. Edgar Trammell, 840 N. 1200 East, Provo, Utah 84601; James E. Young, 2080 E. 4675 South, Salt Lake City, Utah 84117; James R. Chidester, 5780 W. 9600 North; Ralph S. Walker, 9767 N. 6530 West, both of Highland, Utah 84003

[21] Appl. No.: 274,182

[22] Filed: Jun. 16, 1981

[51] Int. Cl.³ ............................................. A61M 16/02
[52] U.S. Cl. ............................................... 128/205.26
[58] Field of Search .................. 128/205.26, 272, 1 B, 128/295, 298, 299, 207.12, 201.23, 247, 201.26, 201.29, 202.19, 202.12, 205.25; 285/DIG. 22, 162, 158, 200, 423, 205; 403/194, 199, 201; 16/2, DIG. 41, 108, 109; 222/569, 105; 239/600

[56] References Cited

U.S. PATENT DOCUMENTS

| | | | |
|---|---|---|---|
| 2,180,960 | 11/1939 | Kennedy | 285/DIG. 22 |
| 2,371,965 | 3/1945 | Lehmberg | 128/205.25 |
| 2,508,050 | 5/1950 | Valente | 128/205.26 |
| 2,764,152 | 9/1956 | Osterberg | 128/205.25 |
| 2,853,997 | 9/1958 | Scherck | 128/1 B |
| 3,091,795 | 6/1963 | Budwig | 16/2 |
| 3,552,391 | 1/1971 | Deaton | 128/205.26 |
| 3,680,557 | 8/1972 | Doniguian | 128/205.26 |
| 4,214,675 | 7/1980 | Schmidt | 222/105 |
| 4,284,242 | 8/1981 | Azalbert | 239/524 |

FOREIGN PATENT DOCUMENTS

| | | | |
|---|---|---|---|
| 2001535 | 9/1969 | France | 285/158 |
| 1358379 | 7/1974 | United Kingdom | 128/272 |

*Primary Examiner*—Lee S. Cohen
*Assistant Examiner*—Harry J. Macey
*Attorney, Agent, or Firm*—Terry M. Crellin; B. Deon Criddle

[57] ABSTRACT

A disposable hood of unitary one-piece construction for maintaining a desired gas atmosphere about the head of a patient incorporates a novel attachment means for connecting a flexible conduit or hose to the hood. The hood itself is a generally bubble-shaped chamber molded of a transparent material with the top and sidewalls being joined in arcuate contours so that there are no sharp corners. Flat extension means extend from the bottom of the hood so as to lie flatwise on the bed, and an arcuate ballast member is adapted to fit closely around the hood and on the flat extension means to hold the hood in position on the bed.

8 Claims, 5 Drawing Figures

DISPOSABLE HOOD

BACKGROUND OF THE INVENTION

1. Field

The present invention relates to apparatus for maintaining a desired gas atmosphere about the head of a patient, especially an infant patient.

2. State of the Art

In many instances it is important to administer oxygen to patients and, particularly infant patients, during hospital care. Oxygen has been conventionally applied to small infants within incubators in controlled amounts. However, the environment in the incubator is subject to undesirable fluctuation during numerous manual care of the infant.

Various hoods and face masks have been proposed to fit over the head of the infant. See, for example, U.S. Pat. Nos. 3,552,391 and 4,022,200 and the references cited therein. Such hoods and masks have been rather cumbersome devices which inhibited quick easy access to the patients head. These devices were rather costly and thus could not be discarded after use, but had to be cleaned and sterilized for further use with a different patient. In spite of such cleaning and sterilization, cross contamination and nosocomial infections were common with the reusable hoods.

3. Objectives

A principal objective of the present invention is to provide an inexpensive disposable hood which is easily and quickly removable from the head of the patient when required but which is otherwise securely held about the patient's head. Another objective is to provide a generally compact hood having a shape such as to minimize the possibility of the patient's mouth or chin from coming into contact with the hood. A further objective is to mold the hood from an optically clear material and shape the hood so that the sides and the top are joined in arcuate contours with no sharp corners to distort the image seen through the hood. An additional objective is to provide a novel attachment means and diffuser for connecting a flexible hose or conduit to the hood and wherein the attachment means and diffuser does not extend significantly into the patient head area within the hood.

SUMMARY OF THE INVENTION

The above objectives are achieved in accordance with the present invention by providing an inexpensive, disposable hood molded from an optically clear plastic. The hood is of a unitary, one-piece construction having a generally bubble-like shape in which the top and sidewalls are joined in arcuate contours so that there are no sharp corners to distort the image of the patient's head. The bottom side of the hood is open and adapted to rest on the bed on which the patient is lying. Flat extension means are provided extending from the lateral and back edges of the open bottom side of the hood so that the extension means lie flatwise on the bed. In accordance with one aspect of this invention an arcuate ballast member is, provided which is adapted to fit closely around the lateral and back edges of the open bottom side of the hood. The ballast member lies over the flat extension means to hold the flat extension means flatwise on the bed under the weight of the arcuate ballast member.

An opening is provided in the forward sidewall of the hood of fit over the neck of a patient whose head is positioned within the hood. Preferably, a bead of soft cushion-like material is formed around the perimeter of the neck opening. The forward sidewall is uniquely shaped as will be fully described hereinafter to minimize the possibility of the patient's mouth or chin from coming into contact with the hood. An aperture is provided in the back sidewall of the hood and a novel, unique attachment means and diffuser, which will be fully described hereinafter, are provided for connecting a flexible hose or conduit to the hood.

Additional objects and features of the invention will become apparent from the following detailed description taken together with the accompanying drawings.

THE DRAWINGS

A preferred embodiment of the invention representing the best mode presently contemplated of carrying out the invention is illustrated in the accompanying drawings, in which.

DETAILED DESCRIPTION OF THE ILLUSTRATED EMBODIMENTS

Figure 1:
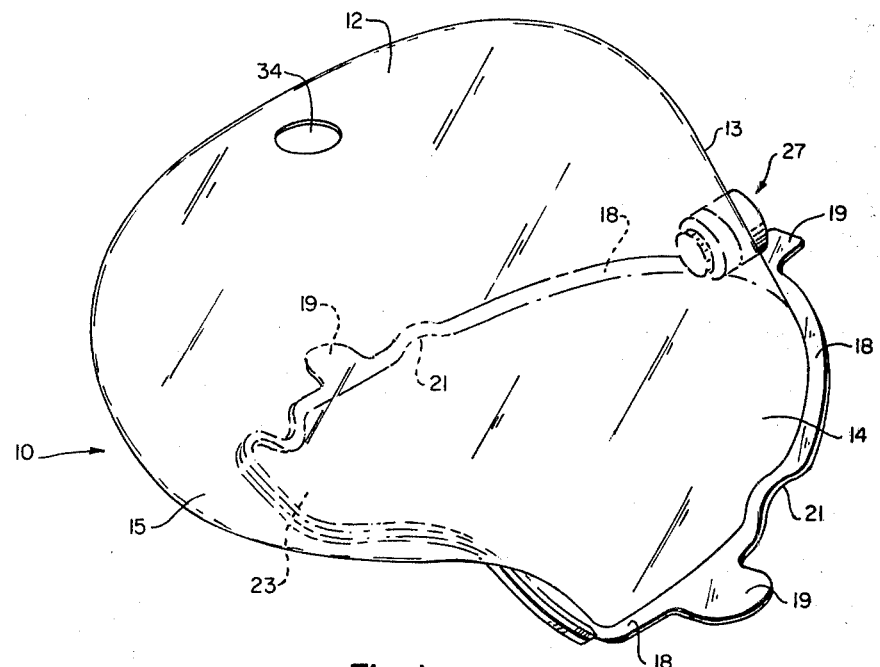
FIG. 1 is a pictorial view of a disposable hood in accordance with the invention.
Figure 2:
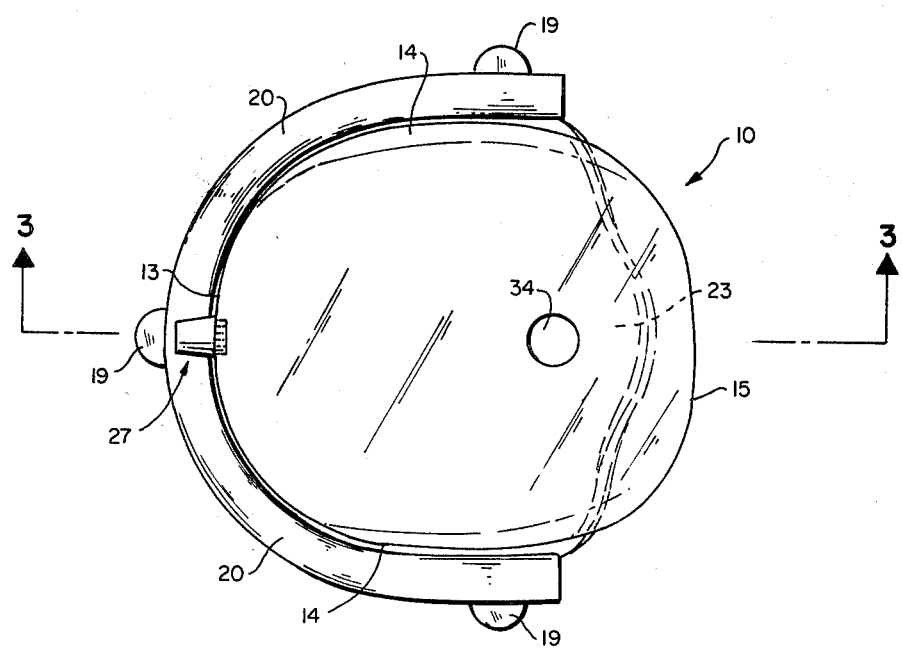
FIG. 2 is a top view of the hood of FIG. 1.

In accordance with the invention, a disposable hood is shown generally by the numeral 10 in the drawings. The hood 10 is designed for use to cover the head 11 of a patient, such as an infant, as the patient is lying . a bed, bassinette, incubator, etc. While the hood of tue present invention finds great applicability with use with infant patients, it is to be understood that the hood could also be used with larger adult patients if desired. Of course, the hood for a larger adult patient would be of a larger overall size than a hood for an infant.

The disposable hood 10 is of unitary, one-piece construction comprising a generally bubble-shaped chamber molded of a transparent, optically clear material such as cellulose acetate butyrate plastic or other optically clear plastic material. The hood 10 has a top 12, back sidewall 13, two side sidewalls 14 and a front sidewall 15. The top 12 has an arcuate arched shape, and the top 12 and the sidewalls 13, 14 and 15 are jointed together in arcuate contours so that there are no sharp corners. The arcuate or bubble-like shape of the hood 10, without any sharp corners, allows clear sight of the patients head at any angle with minimum distortion of the image.

The bottom side 16 of the arcuate, generally bubble-shaped hood 10 is open and adapted to rest on the bed 17 on which the patient is lying. Preferably, as illustrated, a flat ledge 18 extends outwardly from the bottom edges of the lateral sidewalls 14 and the back sidewall 13 in the same plane as the bottom side of the hood 10. The flat ledge 18 is adapted to lie flatwise against the bed 17 as well as add dimensional strength and stability to the bottom edges of the sidewalls 13 and 14. Flat extension means are provided extending from the lateral and back edges of the open bottom side of the hood 10, with the flat extension members being adapted to lie flatwise on the bed 17. The flat extension members can be tabs 19 which extend from the bottom edges of the hood 10 as illustrated, or the flat ledge 18 could be made broad enough to make a continuous flat extension completely around the lateral and back sidewalls of the hood 10. The flat extensions, such as the tabs 19, are used in anchoring the hood to the bed 17.

Safety pins or tape can be utilized to secure the tabs 19 to the bed. Preferably, however, an arcuate ballast member 20 is provided to hold the hood 10 securely on the bed 17. The ballast member 20 has a generally horseshoe shape adapted to fit closely around the back and lateral edges of the bottom side 16 of the hood 10. The ballast member 20 is preferably made of a heavy substance such as a metal rod. Advantageously, a plastic coating can be applied over the external surfaces of the ballast member 20 when the ballast member 20 is made of a metal other than stainless steel. This will prevent corrosion of the metal material. The horseshoe-shaped ballast member 20 lies on the flat extension means such as the tabs 19 to hold the flat extension means flatwise on the bed under the weight of the ballast member 20.

Figure 3:
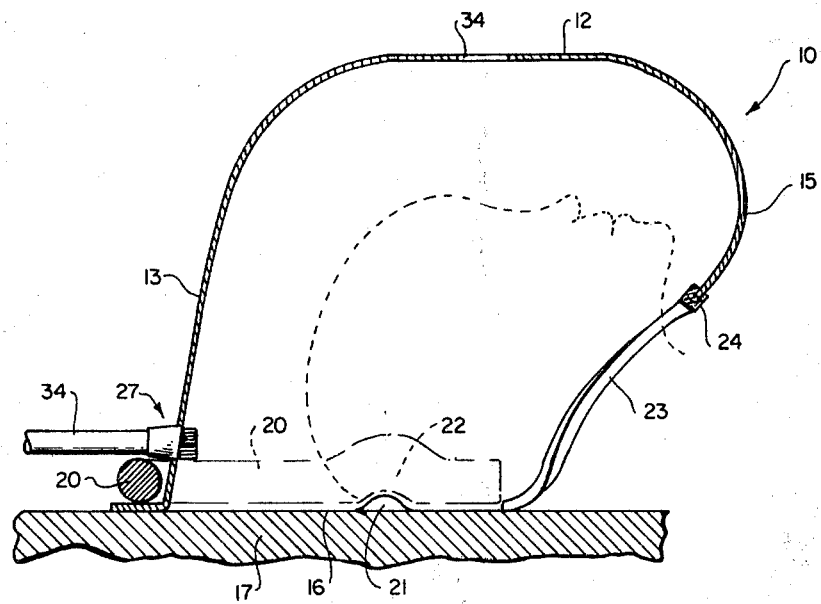
FIG. 3 is a cross-sectional view taken along line 3—3 of FIG. 2.

In the preferred embodiment of the apparatus of the present invention as illustrated, at least one upwardly extending recess or opening 21 is formed in the sidewalls 14 of the hood 10 from the lateral edges of the open bottom side 16 of the hood 10. As illustrated an upwardly extending recess 21 is formed in each of the side walls 14. The recesses 21 are arch shaped and open at their bottoms. As shown in FIG. 3, the ballast member 20 also has upwardly extending arches 22 which are adapted to align with the corresponding recesses 21 in the sidewalls 14 of the hood 10 when the ballast member 20 is in its proper position around the back and lateral edges of the bottom side 16 of the hood 10. The recesses 21 in the hood 10 and corresponding arches in the ballast member 20 permit medical tubing and other diagnostic conduits such as electrical wires which may be attached to probes or other equipment within the chamber defined by the hood 10 to pass outwardly from the hood 10.

A generally arch-shaped opening 23 is provided in the forward or front sidewall 15 of the hood 10. The opening extends upwardly from the open bottom so that the hood 10 can be placed over the patient's head and neck, with the patient's neck extending through the opening 23. As illustrated, the forward sidewall 15 preferably has a shape which in a longitudinal cross-section as shown in FIG. 3 has the general shape of a question mark, with the sidewall 15 curving downwardly in a continuous curve from the top 12. The sidewall continues to curve inwardly and then reverses the curve to again curve downwardly. The opening 23 for the patient's neck is formed in the lower portion of the inwardly and downwardly curving portions of the forward sidewall 15. The neck opening 23 has an open bottom and as mentioned above is generally shaped like an arch. This allows the arch-shaped opening 23 to be readily placed over and around the patient's neck. As illustrated, a bead 24 of ralatively soft, cushion-like material is advantageously formed around the perimeter of the neck opening 23 so as to cover the otherwise raw edge of the neck opening 23 in the sheet plastic of the hood 10. Preferably, an elongate piece of foamed plastic material such as resilient foamed polyurethane is fit over and attached to the edge of the opening 23.

Figure 4:
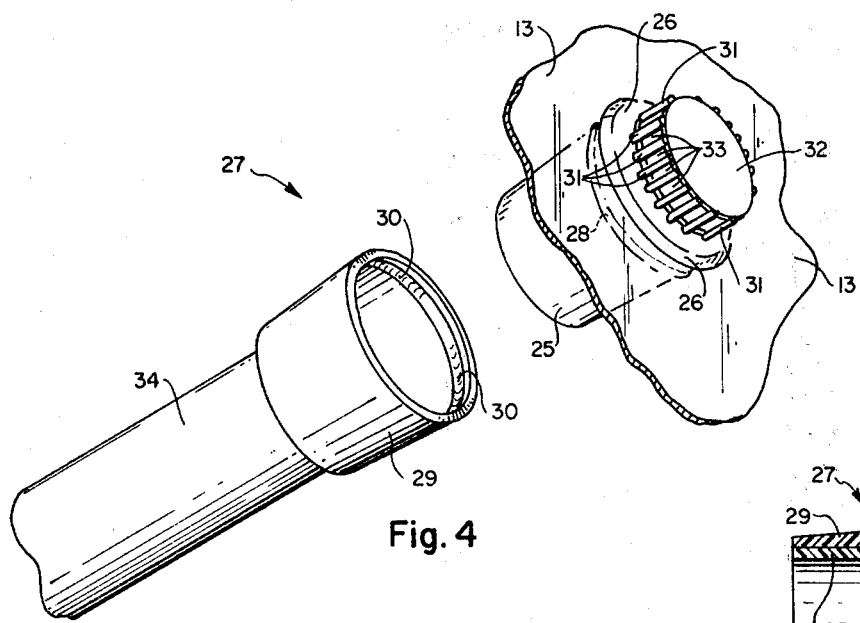
FIG. 4 is a partial exploded view showing the connection of the attachment member to the hood.
Figure 5:
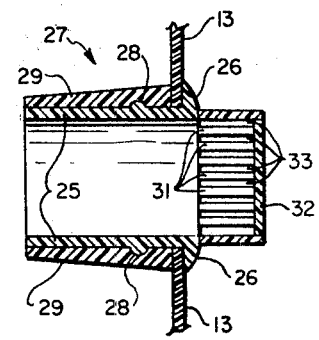
FIG. 5 is a cross-sectional view through the attachment member of FIG. 4.

Novel and unique attachment means shown generally by the number 27 are provided for connecting a flexible conduit or hose to the hood 10. As will be evident, the attachment means is ideally suitable for connecting a flexible conduit or hose to any containment device such as an oxygen tent or hood whereby a gaseous composition can be fed through the conduit or hose to the containment device. As best illustrated in FIGS. 4 and 5, the attachment means comprises a first, generally cylindrical member 25 having a flange 26 extending radially around the one end portion of the cylindrical member 25. The generally cylindrical outer surface of the first member 25 is tapered in a direction from the one end thereof to which the flange 26 is attached towards the other end whereby the outer diameter of the first cylindrical member 25 at the other end is less than the outer diameter thereof at the one end to which the flange 26 is attached. The amount of taper in the outer surface of the first cylindrical member 25 is preferably about 2 to 5 millimeters in 200 millimeters along the longitudinal direction thereof. The inner surface of the hollow cylindrical first member 25 is preferably adapted to be connected to a conventional 15 millimeter tubing connection used in hospitals. Accordingly, the generally cylindrical inner surface of the first member 25 tapers oppositely to the taper of the outer surface, i.e., the diameter of the inner surface at the one end of the member 25 to which the flange 26 is attached is less than the corresponding diameter at the other end thereof. The amount of taper in the inner surface of the first member 25 is preferably about 3.5 to 6.5 millimeters in 200 millimeters along the longitudinal direction. The first cylindrical member also has a raised annular ring 28 around its outer surface with the ring 28 being spaced from the one end of the cylindrical member 25 to which the flange 26 is attached. Preferably the ring 28 is spaced from the inside surface of the flange 26 by about 1 to 3 millimeters. The width of the ring 28 is preferably about 1 to 3 millimeters with the depth of the ring 28 being about 0.1 to 0.5 millimeters.

A second generally cylindrical member 29 is adapted to be received telescopically over the outer surface of the first cylindrical member 25. For that purpose the inside generally cylindrical surface of the second member 29 has the same taper as the taper in the outer surface of the first member 25. Thus, the second member 29 can be telescopically received over the first member 25 as clearly shown in FIG. 5, and when so received, the inside surface of the second member 29 and the outer surface of the first member nest snugly adjacent each other with one end of the second member being positioned adjacent to the flange 26 on the first member 25 as shown in FIG. 5. An annular recess 30 is provided adjacent to one end of the second member 29 such that when the second member 29 is telescopically fit over the first member 25 as shown in FIG. 5, the one end of the second member 29 is deflected over the raised annular ring 28 on the first member 25, with the raised annular ring 28 snapping into engagement with the annular recess 30 in the second member 29. The interengagement of the annular ring 28 in the annular recess 30 locks the first member 25 and second member 29 firmly together in their telescopic position relative to each other. The outer generally cylindrical surface of the second cylindrical member 29 is also tapered with the largest diameter being at the one end which is positioned adjacent to the flange 26 and tapering to a smaller diameter at the other end thereof. The amount of taper is preferably from about 3 to 10 millimeters in 200 millimeters along the longitudinal direction of the member 29. The taper in the outer cylindrical surface of member 29 accommodates the attachment of a hose or hose attachment thereto. The diameter of said other end of member 29 is preferably such that a 22 millimeter tubing can be engaged thereon.

In a preferred embodiment of the attachment means 27 as illustrated, a plurality of elongate fingers 31 project from the otherwise exposed outer end face of the flange 26 on the one end of the first member 25 with a flat diffusion member or plate 32 being attached to the outer ends of the fingers 31 such that the flat plate 32 is spaced from and generally parallel to the otherwise exposed outer end face of the flange 26. The flat plate 32 forms a cover plate over the open inner cylindrical portion of the cylindrical member 25 and spaced therefrom such that a plurality of diffuser openings 33 are formed around the flat plate 32 between adjacent fingers 31.

The attachment means 27 is adapted to be connected to a containment device such as the hood 10 shown in the drawings by slipping the first member 25 through an opening or aperture in the containment device such as an opening in the back sidewall of the hood 10 from the inside of the containment device, i.e., the hood 10, so that the flange 26 on the one end of the first member 25 of the attachment means 27 abuts the inside surface of the containment device or hood 10. The second member 29 then fits over the extending other end of member 25 into the telescopic position shown in FIG. 5. The perimeter of the opening in the containment device or hood 10 is then held firmly between the flange 26 on the first member 25 and the one end of the second member 29 positioned adjacent to the flange 26. By proper positioning of the annular ring 28 in the first member and the annular recess in the one end of the second member 29, proper spacing is provided for the perimeter of the opening to which the attachment means 27 is attached. It is desirable to position the annular ring and recess such that the perimeter of the opening in the containment device will be held firmly between the end of the member 29 and the flange 26.

The attachment means 27 is particularly advantageous when used with the hood 10 as illustrated. The attachment means 27 does not extend significantly into the area within the hood 10, and, thus, the patient's head is not likely to come into contact with the attachment means 27. Gas such as oxygen is admitted to the hood 10 from a flexible hose or conduit 34 under optimum conditions. The gas is diffused through the diffuser openings 33 to flow outwardly in all directions from the flat plate 32 and not into direct impingement with the back of the head of the patient. The flat plate 32 and fingers 31 further act as a muffler to muffle the sound of the gas entering the hood 10.

In the preferred embodiment as illustrated, a second aperture 34a is formed in the top portion of the hood 10 for ventilation of gases therefrom as well as for access for instruments such as a thermometer.

It is to be understood that the present disclosure, including the detailed description of a preferred embodiment which represents the best mode presently contemplated of carrying out the invention, is made by way of example and that various other embodiments are possible without departing from the subject matter coming within the scope of the following claims, which subject matter is regarded as the invention.

We claim:

1. A disposable hood of unitary one-piece construction for maintaining a desired gas atmosphere about the head of a patient, said hood comprising
   a generally bubble-shaped chamber comprising side, forward and back sidewalls and a top, said sidewalls and top being molded from transparent, optically clear material, with the sidewalls being joined to themselves and to the top in arcuate contours so that the hood has no sharp corners;
   a substantially open bottom side for the generally bubble-shaped hood, said bottom side being adapted to rest on the bed on which the patient is laying;
   flat extension means extending from the lateral and back edges of the open bottom side of said hood so that the flat extension means are adapted to lie flatwise on the bed;
   an opening in the forward sidewall of said hood which is adapted to fit over the neck of a patient whose head is positioned in said hood, with the forward sidewall being formed so as to curve in the general shape of a question mark curving continuously downwardly then inwardly and then downwardly, with the opening for the patient's neck being formed in the lower portion of the inwardly and downwardly curving portions of said forward sidewall;
   an aperture in the back sidewall of said hood; and
   an attachment means for connecting a flexible conduit or hose to said aperture.

2. A disposable hood in accordance with claim 1 wherein a bead of relatively soft cushion-like material is formed around the perimeter of said opening in which the neck of the patient is to be positioned.

3. A disposable hood in accordance with claim 1 wherein a second aperture is formed in the top of said hood for ventilation of gases therefrom as well as access for instruments such as a thermometer.

4. A disposable hood in accordance with claim 1, wherein the attachment means for connecting the flexible conduit or hose to said aperture comprises:
   a first generally cylindrical member having a flange extending radially around one end portion thereof, said first member being inserted through said aperture from the inside of said hood so that said flange on said one end of said first member abuts the inside surface of said hood, said first member further having a generally cylindrical outer surface which is tapered in a direction from said one end thereof towards the other end, whereby the outer diameter of said first cylindrical member at said other end is less than the outer diameter thereof at said one end adjacent to said flange, and said first member also having a raised annular ring around the circumference thereof, said ring being spaced from said one end of said first cylindrical member; and
   a second generally cylindrical member having an inside cylindrical surface that tapers from one end of said second member towards the other end thereof such that the second member can be telescopically received over the first member from said other end of said first member, whereby when said second member is received telescopically over said first member, the inside surface of said second member and the outer surface of said first member rest snugly adjacent each other, said second member further having an annular recess adjacent said one end thereof such that when said second member is telescopically fit over said first member, said one end of said second member is deflected over the raised annular ring on said first member, with the raised annular ring snapping into engagement with the annular recess in said second member, whereby the first and second members are held firmly in their telescopic position and said one end of said second member abuts the outer surface of said hood around the perimeter of said aperture to fix said attachment means firmly to said hood.

5. A disposable hood in accordance with claim 4, wherein a plurality of elongate members project from the otherwise exposed outer end face of said flange on said one end of said first member, and a flat member is attached to the outer ends of said elongate members so that said flat plate is spaced from and generally parallel to the otherwise exposed outer end face of said flange, whereby a plurality of diffuser openings are formed around the flat plate between adjacent elongate members.

6. A disposable hood in accordance with claim 4, wherein the outer diameter of said second member is adapted for connection to a 22 millimeter hose connection and the inner diameter of said first member is adapted for connection to a 15 millimeter hose connection.

7. A disposable hood of unitary one-piece construction for maintaining a desired gas atmosphere about the head of a patient, said hood comprising
 a generally bubble-shaped chamber comprising side, forward and back sidewalls and a top, side sidewalls and top being molded from transparent, optically clear material, with the sidewalls being joined to themselves and to the top in arcuate contours so that the hood has no sharp corners;
 a substantially open bottom side for the generally bubble-shaped hood, said bottom side being adapted to rest on the bed on which the patient is lying;
 flat extension means extending from the lateral and back edges of the open bottom side of said hood so that the flat extension means are adapted to lie flatwise on the bed;
 an opening in the forward sidewall of said hood which is adapted to fit over the neck of a patient whose head is positioned in said hood;
 an aperture in the back sidewall of said hood;
 an attachment means for connecting a flexible conduit or hose to said aperture; and
 an arcuate ballast member adapted to fit closely around the lateral and back edges of the open bottom side of said hood and over said flat extension means to hold the flat extension means flatwise on the bed under the weight of said arcuate ballast member.

8. A disposable hood in accordance with claim 1, wherein at least one upwardly extending recess is formed in the sidewalls of said hood from the lateral edges of the open bottom side of said hood so that tubing and other elongate diagnostic conduits can pass outwardly from the hood, with said arcuate ballast having upwardly extending arches which align with corresponding recesses in the sidewalls of said hood.

* * * * *